(12) United States Patent
Béland et al.

(10) Patent No.: US 8,551,543 B2
(45) Date of Patent: Oct. 8, 2013

(54) SYMBIOTIC MAPLE PRODUCT COMPOSITIONS AND METHODS

(75) Inventors: Geneviève Béland, Saint-Hyacinthe (CA); Julie Barbeau, Boucherville (CA); Ismail Fliss, Sainte-Foy (CA)

(73) Assignee: Fédération des Producteurs Acéricoles du Québec, Longueuil (CA)

( * ) Notice: Subject to any disclaimer, the term of this patent is extended or adjusted under 35 U.S.C. 154(b) by 0 days.

(21) Appl. No.: 13/202,668

(22) PCT Filed: Mar. 5, 2010

(86) PCT No.: PCT/CA2010/000308
§ 371 (c)(1),
(2), (4) Date: Oct. 11, 2011

(87) PCT Pub. No.: WO2010/099617
PCT Pub. Date: Sep. 10, 2010

(65) Prior Publication Data
US 2012/0027735 A1 Feb. 2, 2012

Related U.S. Application Data

(60) Provisional application No. 61/158,151, filed on Mar. 6, 2009.

(51) Int. Cl.
*A01N 65/00* (2009.01)
(52) U.S. Cl.
USPC ........................................................ 424/771

(58) Field of Classification Search
None
See application file for complete search history.

(56) References Cited

U.S. PATENT DOCUMENTS

2007/0160589 A1* 7/2007 Mattson ..................... 424/93.45
2008/0026441 A1* 1/2008 Fournier et al. ............... 435/139

FOREIGN PATENT DOCUMENTS

| CA | 2594937 | 1/2008 |
| WO | WO 2009086045 | 7/2009 |

OTHER PUBLICATIONS

Cochu A. et al, Maple sap as a rich medium to grow probiotic lactobacilli and to produce lactic acid. Lett. Appl Microbiol. December 200, vol. 47, No. 6, pp. 500-507, ISSN 1472-765X.
PCT—International Search Report (ISR)—PCT/CA2010/000308 (Form PCT/ISA/210)—Jul. 29, 2010—4 pages.

* cited by examiner

Primary Examiner — Suzanne M Noakes
Assistant Examiner — Stephen Chong
(74) Attorney, Agent, or Firm — Benoît & Côté inc.

(57) ABSTRACT

The present invention relates to novel maple product compositions. In particular, the present invention relates to new compositions comprising maple sap, maple concentrate, maple syrup or diluted maple syrup, and probiotics, prebiotics or combinations thereof. The present invention also discloses methods for the production of maple based products, including functional drinks, comprising a composition comprising maple sap, maple concentrate, maple syrup or dilutated maple syrup, and probiotics, prebiotics or combinations thereof, as a vehicle for the delivery of probiotics and prebiotics to the gastrointestinal tract.

20 Claims, 5 Drawing Sheets

SYMBIOTIC MAPLE PRODUCT COMPOSITIONS AND METHODS

This application claims priority from U.S. Provisional Patent Application No. 61/158,151 filed on Mar. 6, 2009.

FIELD OF THE INVENTION

The present invention relates to novel maple product compositions. In particular, the present invention relates to new compositions comprising maple sap, maple concentrate or maple syrup and probiotics, prebiotics or combinations thereof, and to methods for the production and stabilisation of a functional drink comprising a composition comprising maple sap, maple concentrate, maple syrup or diluted maple syrup, on the first hand, and probiotics, prebiotics or combinations thereof, on the second hand, as a vehicle for the delivery of probiotics and prebiotics to the gastrointestinal tract.

BACKGROUND OF THE INVENTION

There are a number of health drinks in the market containing probiotics and/or prebiotics. Virtually all major brands of commercial milk products have at least one milk product enriched with probiotics and/or prebiotics such as Danone DanActive™, Astro Biobest Maximmunité™ and Natrel Pro™. Generally speaking the market for probiotics has two parts: (1) food products (especially food products requiring refrigeration) and (2) supplements. There are generally two categories of the mentioned food products: (A) dairy culture based products such as yogourts, and (B) food products with a lactic ferment base other than those based on a dairy culture. Dairy culture based products according to category (A) include solid food products (such as BULGARIA YOGURT™ or LG21™ of Meiji Dairier, or CASPIAN SEA YOGURT™ of Fujicco Co.) and liquid food products such as liquid yogurt products. Food products with a lactic ferment base other than those based on a dairy culture according to category (B) include drinks based on lactic bacteria from milk such as YAKULT™ marketed by Yakult Honsha; drinks based on other forms of lactic bacteria such as LABRE™ marketed by Kagome; and other products based on lactic ferment such as soy milk yogurt marketed by Spyafarm. The supplements generally include tablets (such as BIFINA™ brand products marketed by Morishita-Jinta) and liquids such as lactic bacteria from algae.

Natural spring waters and fruit juices are sold in pure form or flavoured with some enrichment minerals and/or vitamins. However, none are enriched with probiotics and/or prebiotics, mainly because the chemical composition of the water source does not support this type of enrichment.

The neutral pH of milk, its fat and protein content are the elements that provide a protective effect and allow the probiotic action in the gastro-intestinal system. The acidity of fruit juice does not allow for the inoculation and the survival of probiotics.

It is known that maple sap is a source of naturally distilled, pure water. It is also known in the art that the water found in sap may be removed, for example, during the production of maple syrup in order to market and sell the water as non-carbonated, "pure and natural distilled and condensed Maple Steam" (for example, available as VERMONT MAPLE WATER™ from Vermont Maple Water, Inc., East Arlington, Vt. 05252).

Canadian patent application No. 2,594,937 ('937 application) discloses the use of maple sap as a medium in a bioreactor to grow probiotics under continuous agitation at 37° C. and in the presence of a substrate rich in nitrogen, such as soy drink. The '937 application does not suggest or teach the use of pure, non-supplemented sap, maple concentrate, maple syrup or diluted maple syrup in a composition as a delivery vehicle for probiotics, prebiotics or a combination thereof.

Using maple sap, maple concentrate, maple syrup or diluted maple syrup in a functional drink as a delivery vehicle for probiotics and/or prebiotics present a number challenges that are not solved by the prior art, namely: (1) to ensure the survival of probiotic strains inoculated in the sap, maple concentrate, maple syrup or diluted maple syrup; (2) to select commercial probiotic strains that are resistant to environment; (3) to inoculate sufficient quantity of probiotic strains in the composition to maintain a good survival rate and maintain the organoleptic characteristics and the environment; (4) to produce a product with a reasonable shelf-life and (5) to maintain a good survival rate of probiotics in the gastrointestinal (stomach and small intestine) system of the subject ingesting the symbiotic composition. Several factors in the gastrointestinal system such as bile salts, enzymes, pH and temperature decrease and even go so far as to inhibit the action of probiotics. It is an object of this invention to overcome these challenges.

It is an object of the present invention to provide a drink that provides health benefits. Until the invention presented herein, the enrichment of maple sap, maple concentrate, maple syrup or diluted maple syrup with prebiotics and probiotics was never implemented.

BRIEF SUMMARY OF THE INVENTION

A novel composition comprising a maple sap, maple concentrate, maple syrup or diluted maple syrup and at least one of a probiotic, a prebiotic or a combination thereof has now been developed, which is useful as a health composition.

Thus, in one aspect of the present invention a composition suitable to be delivered to a mammalian gut, comprising maple sap, maple concentrate, maple syrup or diluted maple syrup and at least one probiotic is provided.

In another aspect of the present invention a composition suitable to be delivered to a mammalian gut, comprising maple sap, maple concentrate, maple syrup or diluted maple syrup and at least one prebiotic is provided.

In yet another aspect of the present invention a composition suitable to be delivered to a mammalian gut, comprising maple sap, maple concentrate, maple syrup or diluted maple syrup, at least one probiotic and at least one prebiotic is provided.

In still another aspect of the present invention, a functional drink comprising a composition suitable to be delivered to a mammalian gut, said composition comprising maple sap, maple concentrate, maple syrup or diluted maple syrup and at least one of a probiotic, a prebiotic or a combination thereof is provided.

In one aspect a method of producing a composition comprising a maple sap, maple concentrate, maple syrup or diluted maple syrup and at least one of a probiotic, a prebiotic or a combination thereof, is provided.

In another aspect a method of using a composition comprising a maple sap, maple concentrate, maple syrup or diluted maple syrup and at least one of a probiotic, a prebiotic or a combination thereof, is provided.

Advantages of the compositions of the present invention include:

(1) The ability to provide a symbiotic drink with no calories, that is refreshing, hydrating and with added health benefits.

(2) Probiotics and prebiotics provided in a single product (which is not always the case).

(3) The ability to provide probiotic-containing product with a life shelf-life of up to 30 days when kept at 4° C.

(4) The ability to maintain a good survival rate of probiotics in the gastrointestinal system.

(5) The delivery of probiotics and/or prebiotics as part of a natural product from a plant source, with the positive image characteristics of such a product.

(6) Providing a natural, plant based drink that offers an alternative source of prebiotics and propbiotics to lactose intolerant consumers, where the prebiotic or probiotic strain has not been cultivate in a lactose source.

(7) Superior product in terms of providing a matrix or base that is enriched with natural nutrients (such as simple of complex sugar carbons, minerals, vitamins, phenol, amino acids, organic acids, peptides, phytohormones) for providing probiotic and prebiotic active elements.

These and still other objects and advantages of the present invention will be apparent from the description which follows.

BRIEF DESCRIPTION OF THE DRAWINGS

The present invention will become more fully understood from the detailed description given herein and from the accompanying drawings, which are given by way of illustration only and do not limit the intended scope of the invention.

DETAILED DESCRIPTION OF THE INVENTION

A novel composition is provided. In one aspect, the composition of the present invention comprises a maple sap, maple concentrate, maple syrup or diluted maple syrup and at least one of a probiotic, a prebiotic or a combination thereof. In another aspect the present invention provides for a method of producing a composition comprising a maple sap, maple concentrate, maple syrup or diluted maple syrup and at least one of a probiotic, a prebiotic or a combination thereof. In yet another aspect, the present invention provides for a method of using a composition comprising a maple sap, maple concentrate, maple syrup or diluted maple syrup and at least one of a probiotic, a prebiotic or a combination thereof.

The compositions of the present invention can be used to produce improved beverages, foods, and feeds, and other products for increasing levels of healthful bacteria and/or prebiotics in mammalian guts.

For the purpose of this application, the following terms have the following meanings:

"Probiotic" is defined by the United Nations Food and Agricultural Organization and the World Health Organization as "live microorganisms, which, when administered in adequate amounts, confer a health benefit on the host". "Prebiotic" means any substance that acts as a substrate to any relevant probiotic, or that otherwise assists in keeping the relevant probiotic alive or stimulates its growth, and includes mucopolysaccharides, oligosaccharides, polysaccharides, amino acids, vitamins, nutrient precursors and proteins. The association of probiotics with prebiotics gives rise to compositions/products generally defined by the term "symbiotic".

Maple sap is a naturally occurring, unprocessed crystal-clear liquid, having the consistency and clarity of water, which derives from the sugar maple tree. Maple sap has sugar content that is anywhere from approximately 1° to 5° Brix. The sugar content in sap depends on the harvest period, temperature, exposure to sun, the maple region, size and age of the maple. The harvest of sap is made in the spring, between March and April, when the temperature is below the freezing point during the night and greater than zero degrees Celsius during the day. The majority of the sugar content in maple sap comprises sucrose and glucose. The remainder of the maple sap content (95-98%) consists of naturally occurring water and very small amounts of organic acids, a portion of which is responsible for the maple flavor. The nitrogen content in sap is 0.25% in the form of organic nitrogen from amino acids and proteins. The sugars are sources of carbon that may be greatly appreciated by the probiotic strains. Arabinogalactan was also identified in the Maple Products (Desjardins, Y. 2007. Caractérisation de produits d'érable lyophilisés. In Québec: INAF/Université Laval. 94 pages). Arabinogalactan is a polysaccharide widely used as prebiotic to stimulate the growth of probiotics in the gastrointestinal tract. According to the same publication, other products were also found as organic acids, vitamins, minerals, flavonoids and phenolic compounds. The pH of maple sap ranges from 6.5 to 7 with a tendency to decrease towards the end of the sugaring season. Microbial contamination of the sap is mainly composed of Pseudomonas type varies from $10^2$ to $10^6$ increasing to the end of the season. Maple syrup is the viscous liquid obtained by concentration and heat treatment of maple sap.

"Maple concentrate" is maple sap concentrated at, for example, 10° Brix having passed through a reverse osmosis membrane which has the effect of concentrating the sugars and nutrients from the maple sap. The concentrated sap may then be routed to produce maple syrup.

"Diluted maple syrup" is maple syrup diluted at different concentrations (66° Brix to 2° Brix) with a sterilized solution such as water or other solvents (such as juice, milk or any other alimentary liquid).

"Maple product" in this document refers to maple sap, maple concentrate or maple syrup, and any product derived from maple sap, maple concentrate, maple syrup or diluted maple syrup.

As used in this specification and the appended claims, the singular forms "a," "an," and "the" include both the singular and the plural unless the context clearly dictates otherwise. For example, a composition containing "a probiotic" includes a composition having one probiotic or two or more probiotics, and "a prebiotic" includes a prebiotic or two or more prebiotics. Each of the terms "includes," "include," "comprises" and "comprise" means "includes at least." For example, "a prebiotic comprising inulin" means the prebiotic includes at least inulin; it may also include other prebiotics and/or other substances.

The present invention comprises one or more of the following: (a) a novel composition comprising a maple sap, maple concentrate or maple syrup and at least one of a probiotic, a prebiotic or a combination thereof, (b) a novel drink comprising a composition comprising a maple sap, maple concentrate or maple syrup and at least one of a probiotic, a prebiotic or a combination thereof and (c) methods of producing and using composition comprising a maple sap, maple concentrate, maple syrup or diluted maple syrup and at least one of a probiotic, a prebiotic or a combination thereof.

Probiotics that may be used to practice the invention are microorganisms that can survive in maple products and benefit mammalian (particularly human) health, particularly gastrointestinal health. The probiotic that may be used to practice the invention includes one or more of a *Lactobacilli* and *Bifidobacteria*, for example. Specific probiotics that may be used include, but are not limited to, one or more of *Lactobacillus* (abbreviated "L") *rhamnosus, L. acidophilus, L. plantarum, L. reuteri, L. curvatus, L. bulgaricus, L. grasseri, L. casei, L. fermentum, L. caveasicus, L. helveticus, L. lactis, L. salivarius, L. brevis, L. leichmanni, L. cellobiosus, L. buchneri, Bifidobacterium* (abbreviated as "B,") *laterosporus, B. lactis* Bb12, *B. longum, B. breve, B. subtilus, L. sporogenes* (also known as *Bacillus coagulans*), *pediococcus acidilactici, pediococcus pentosaceus, enterococcus faecium, B. adolescentis, B. infantis, B. thermophilum, B. animalis*, and *B. bifidum. Steptococcus thermphilius* may also be used, which is believed to improve lactose digestion and make micronutrients more available to the host. Other probiotics that may be used include *Lactococcus lactis cremoris, S. diacetylactis* and *S. intermedius*. Another example of a probiotic include enterococcus faecalis, and butanoic acid bacterias. It should be noted that the present invention also contemplates the inoculation of the maple products with combinations of microbes that live in symbiosis such as for example cultures of bacteria and yeast for example, as is the case of tibicos, also known as water kefir grains, sugar kefir grains or Japanese water crystals.

In one aspect of the present invention the probiotic strains that may be used to practice the invention include *L. rhamnosus, L. acidophilus, L. plantarum, B. lactis* Bb12 and *B. longum*. In another aspect of the present invention the probiotic strains that may be used to practice the present invention include *L. rhamnosus* and *B. lactis* Bb12.

Commercially available strains of *Lactobacilli* and *Bifidobacteria* may be obtained from Chris Hansen (USA).

The minimum effective dose of probiotics is not precisely known, however, an oral dose of $10^8$ Colony Forming Units (cfu) or more per day may be necessary to achieve health benefits. Enzymes, bile salts, pancreatic secretions, pH, temperature and transit time through the gastrointestinal track will directly affect the survival of probiotics. In general, passage through the digestive system results in 1 log inhibition of probiotics.

Moreover, the concentration of probiotics in a drink or product will be directly linked to the volume of the drink and product consumed. For example, a 100 ml drink inoculated with $10^{10}$ cfu probiotics a probiotic concentration of $10^8$ cfu/ml. After ingestion of the drink, there is a loss of about 1 log, and the consumer would have absorbed $10^7$ cfu in probiotics and provide the health benefits expected. A probiotic concentration of at least $10^8$ cfu/ml ensures that the final amount in the digestive system will be $10^7$ cfu.

Prebiotics that may be used to practice the instant invention comprise one or more of the following (a) an oligosaccharide, (b) a fructo-oligosaccharide ("FOS"), such as a soy fructo-oligosaccharide, inulin or banana fiber, (c) a pectin or pectic polysaccharide, (d) a mannan, such as guar gum, locust bean gum, konjac, or xanthan gum, (e) a pentosan, beta-glucan, arabinan and galactan, such as larch arabinogalactan, (f) serum peptides and (g) mixtures thereof.

FOS are long-chain polysaccharides comprised primarily of fructose monosaccharides bonded together by 1-β-D-fructofuranosyl linkages. Upon ingestion, fructo-oligosaccharides are only partially hydrolyzed as they pass through the mouth, stomach, and small intestine. In the large intestine, they become food for certain probiotics, such as *L. acidophilus* and *B. infantis* and are metabolized into SCFAS, mainly acetic, propionic, butyric, and lactic acids. As a consequence of this fermentation, a considerable amount of bacterial mass is produced. This results in increased numbers of probiotic, a lowered intestinal pH, and is believed to inhibit pathogens. A pH decrease will increase solubility of calcium and other minerals and may enhance the absorption of calcium and magnesium. Illustrative fructo-oligosaccharides include inulin, banana fiber, and soy fructo-oligosaccharides, and are found in honey, beer, onion, asparagus, Chinese chive, maple sugar, oats, and Jerusalem artichoke.

Inulin is produced naturally in an estimated 36,000 or more plants worldwide including onion, asparagus, artichoke, and many cereals. Chicory root and Jerusalem artichoke each contain a significant amount of inulin. In addition to encouraging the growth of probiotics, some animal and human studies suggest that inulin oligosaccharides provide the benefit of enhancing calcium and magnesium absorption in the small intestine.

Some specific prebiotics that may be used to practice the invention include: (1) FOS; (2) short chain FOS; (3) inulin; (4) resistant starch; (5) starches such as starches derived from natural corn starch, (6) larch arabinogalactan, (7) hydrogenated lactose, and (8) serum proteins. Other prebiotics include the galacto-oligosaccharides (GOS), xylo-oligosaccharides (XOS), lactosucrose or lactulose.

In one aspect, the composition according to the instant invention is a symbiotic composition comprising a maple product, a probiotic and a prebiotic. In one aspect the prebiotic complements the probiotic in the symbiotic composition, but the prebiotic may complement another probiotic, such as one present in the intestines but not in the composition.

The inventors discovered that probiotics inoculated in unsterilised sap and concentrate maple could not survive due to the action of the endogenous flora of the sap and concentrate maple. In order to inoculate the sap, maple concentrate, maple syrup or diluted maple syrup with probiotics and expect a survival of the inoculate over a long period of time, it is essential to inactivate endogenous flora (bacteria in the sap) by a sterilization treatment that does not alter the endogeous nutraceutical compounds (intrinsic qualities) of the sap, maple concentrate, maple syrup or diluted maple syrup as the endogenous nutraceutical compounds comprise essential nutrients for the survival of the inoculated probiotics. The inventors tested several thermal processes such as extended 55° C./30 minutes at 121° C./15 minutes coupled with a UV or microfiltration. In one aspect of the present invention the sterilization process which reduces the endogenous flora and maintains the intrinsic qualities of the product (sap, concentrated sap of maple, maple syrup or diluted maple syrup) is a sterilization process comprising continuously combining a mild heat treatment (63° C./20 minutes or 80° C./10 minutes) followed by a microfiltration step on a nylon membrane for example (0.8 m). The sterilization treatment can eliminate the microbial load of treated products including psychotropic, yeasts and molds. On average, endogenous flora reduction of approximately 7 log was obtained and no micro-organism was detected after four months storage at 4° C. The physico-chemical analysis showed that the new sterilization process resulted in only minor changes in terms of product features including a slight decline in total solids and an increase in invert sugar. No changes were observed at the level of pH, which remained stable between 6 and 7 during storage. These minor changes do not affect the integrity of the product, its taste and the survival of probiotics. Maple sap and maple concentrate having been subjected to a sterilization process at high temperatures of around 121° C. for 15 minutes (although lower temperatures are also possible with some microfiltration) provide a medium into which probiotics and prebiotics can be inoculated with a rate of survival comparable to the rate of survival for pasteurised maple sap or maple concentrate as per the process described earlier namely combining a mild heat treatment (63° C./20 minutes or 80° C./10 minutes) followed by a microfiltration step on a nylon membrane for example (0.8 m). It should be understood that maple syrup or diluted maple syrup may also be used provided that these are sterile by virtue of their production method. In a particular aspect of the invention, the sterilization step is followed by a microfiltration step, where the sterilization step involves processing the maple product at a temperature of less than 121° C.

It should be noted that the present invention contemplates the use of the various sterilization methods used in the food industry. The specific temperature and time based food treatment methods described herein are not meant to be exhaustive, but rather indicative that maple based products may be made based on conventional food treatment methods, while based on the discovery of the inventors, providing a medium for survival of probiotics and prebiotics The sugar content of the maple product may affect the viability of the added probiotics. Thus, in one aspect the present invention is a composition comprising a maple product and at least one of a probiotic or a prebiotic or a combination thereof, wherein the maple product has 1° to 20° Brix. In other aspects the present invention is a composition comprising a maple product and at least one of a probiotic or a prebiotic or a combination thereof, wherein the maple product has 1° to 10° Brix. In other aspects the present invention is a composition comprising a maple product and at least one of a probiotic or a prebiotic or a combination thereof, wherein the maple product has 1° to 5° Brix. Studies have shown that probiotics have a rate of survival that is relatively stable with instance of one log after 45 days at 4° C. in a pure maple syrup at 66° Brix, diluted at different sugar concentrations (40, 20, 10 et 2° Brix). A maple based matrix therefore provides an excellent medium for ensuring the survival of probiotics and prebiotics, which behave similarly. In contrast, a significant decrease in the rate of survival is observed in matrices after 15 days of storage at 4° C. in a medium of pure water (loss of between 3 and 5 logs).

It is desirable to provide compositions comprising maple products and at least one of a probiotic or a prebiotic or a combination thereof having a reasonable shelf-life. Thus, in another aspect of the present invention a composition is provided comprising a maple product and at least one of a probiotic or a prebiotic or a combination thereof, wherein said composition has a shelf life of at least 45 days at 4° C.

In other aspects of the present invention, the storage time of the compositions of the invention may be increased by submitting the compositions of the invention to a freezing process. Investigations have shown that the resistance of two matrices of probiotics (LGG and Bb12) to temperature changes (freezing at −20° C. et thawing at 4° C.). No loss in activity in the matrices was observed after thawing. This is because of the maple based medium plays a protective role in the survival of probiotics. The present invention therefore provides a means for enabling the storage and transportation of products containing probiotics or prebiotics in a way that there is a certain tolerance for temperature change.

In one aspect of the instant invention, a symbiotic composition of the invention would comprise of up to $10^{10}$ cfu/ml probiotic and up to 3% prebiotic. In one aspect, the probiotic and prebiotic represent up to 2% of the composition. The composition may be delivered in combination with any other substance or compound, such as enteral food, as long as the other substance or compound does not destroy the ability of the symbiotic composition to confer a beneficial effect. For example, the composition may comprise prebiotics other than those specifically described herein, such as bifidius factor (currently available only from human milk), minerals, vitamins, phytochemicals, enzymes, lactoperoxidase, thiocyanate salt, lactoferrin, gluconic acid, phytochemical, amino acids and/or other substances that may benefit the probiotic of choice or otherwise benefit the subject.

The symbiotic compositions in accordance with the present invention may be used as a functional matrix for other products containing probiotics and/or prebiotics such as for example health drinks which may include mineralized drinks, soya milk based drinks, vinegar based drinks, vegetable based drinks, teas, water containing food supplements, and nourishing drinks. The compositions of the present invention can also be used for beauty products such as shampoos, ointments, beauty creams and the like.

The compositions of the present invention may be ingested orally as a drink. However, the compositions may also be ingested in other formulation such as a tab let, gel, gel capsule, lozenge, pill, or powder.

Any capsule or tablet suitable for at least partially protecting the probiotic as it passes through the stomach, thus allowing a greater amount of probiotic to enter the large intestine than would enter without use of the capsule or tablet, may be used. Such a tablet may have a generally homogenous composition or include individual layers containing the various constituents of the tablet (such as the probiotic and prebiotic).

Having described preferred embodiments of the invention, alterations and modifications within its scope may occur to others. The scope of the invention is not limited to the particular examples, process steps, or materials disclosed as preferred embodiments but is instead set forth in the appended claims and legal equivalents thereof.

Example 1

Processing of Maple Sap

Maple sap, maple concentrate, maple syrup and diluted maple syrup were sterilized by a sterilization process that comprises of continuously combining a mild heat treatment (63° C./20 minutes or 80° C./10 minutes) followed by a microfiltration step on a nylon membrane (0.8 m) followed by a treatment at 63° C. for 15 or 30 minutes.

The sterilization process resulted in an endogenous microbial reduction of approximately 7 log, and no endogenous microorganisms were detected after four months storage at 4° C. Physico-chemical analysis showed that the developed process resulted in only minor changes in terms of product features including a slight decline in total solids and an increase in invert sugar. No changes were observed in the pH level, which remained stable between 6 and 7 during said storage. These minor changes do not affect the integrity of the product, its taste and the survival of probiotics.

This process of cold pasteurisation should be applied to the sap or maple concentrate before the inoculation with probiotics and prebiotics.

Example 2

Maple Sap Enrichment with Probiotics

Commercial strains of the genus *Lactobacillus* (*L. rhamnosus, L. acidophilus* and *L. plantarum*) and *Bifidobacterium* (*B. lactis*) were tested for their ability to survive in water of maple. These strains were obtained from the company Chris Hansen (USA) and used as freeze-dried. Sap previously sterilized by the process of cold pasteurization (Example 1) was inoculated with probiotic strains (alone or in combination) at different concentrations ($10^7$, $10^8$, $10^9$ CFU/ml) with or without added prebiotics.

Example 3

Maple Sap Enrichment with Prebiotics

The effect of enrichment with prebiotics was measured to validate their impact on the rate of survival of the probiotics inoculated as provided in Example 2. Commercial prebiotics tested include arabinogalactan, inulin and serum proteins. The final prebiotic concentrations were 2.5% for serum protein and 2.5% in inulin.

Example 4

Figure 1:
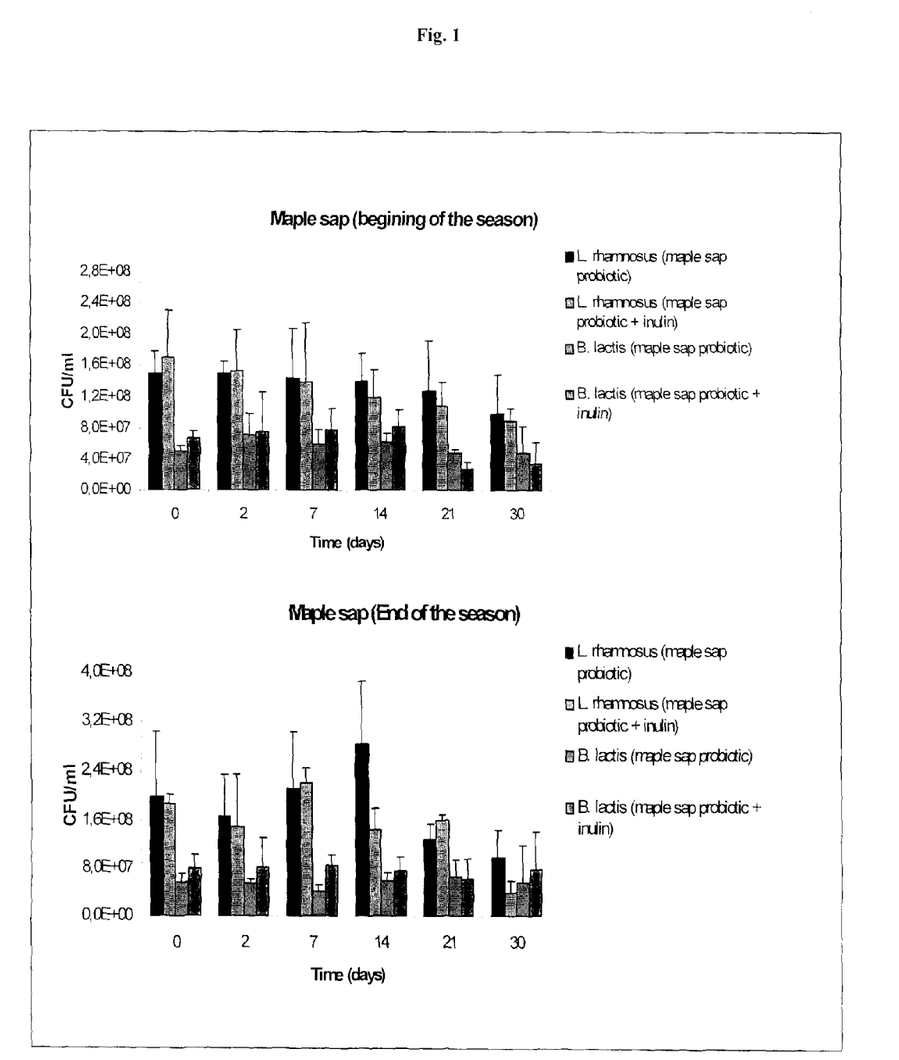
FIG. 1 is an illustration of the storage survival rate of *L. rhamnosus* and *B. lactis* Bb12 in maple sap, with or without added 2% inulin, at 4° C. for 30 days.

Survival Rate of Maple Products Enriched with Probiotics with or without Added Prebiotics Beginning of season and end of season maple products were enriched as per Example 2 and Example 3, stored at 4° C. and tested for probiotic survival at 0, 2, 7 14, 21 and 30 days following incubation with probiotics with or without added prebiotic. Only two probiotics strains were able to survive in water of maple after 30 days at 4° C.: *Lactobacillus rhamnosus* and *Bifidobacterium lactis* Bb12. The results presented in FIG. 1 relate the accounts of both microbial probiotic strains that showed the best survival rates in the sap namely *Lactobacillus rhamnosus* and *Bifidobacterium lactis* Bb12. FIG. 1 clearly illustrates that *B. Lactis* Bb12, although inoculated with a lower initial concentration ($4 \times 10^7$ cfu/ml), is able to survive 30 days of storage at 4° C. both in the presence or absence of the prebiotic inulin. A significant loss was observed after 30 days of storage, which is exceptional given the nature of product inoculated (maple sap concentrate to 2° Brix predominantly sugar). *L. rhamnosus* for its part has demonstrated a lower survival rate with a loss of about 1 log observed at 30 days of incubation. Despite this loss, the final observed concentration remains relatively high and sufficient to exert beneficial effects in the gastrointestinal tract.

Example 5

Physico-Chemical Analysis of Maple Products Enriched with Probiotics

Analyses were performed to measure the impact of the enrichment of maple products with probiotics on the physico-chemical and organoleptic intrinsic character of the product. The analysis conducted included the determination of pH (pH meter Accumet), total solids (transmission at 560 nm using Beckman 96157 Holmium oxide filter spectrophotometer, refractometer Reichert AR200), invert sugar content (Ascensia Contour Glucometer) and the Maillard reaction (spectrophotometer Beckman 96157).

No changes were observed in the total solid content after enrichment with probiotics (2.3% for the sap and 10% for the concentrated maple, maple syrup (66° Brix) or diluted maple syrup at a different concentration.

Analysis of pH in the sap revealed values close to neutrality (7) for the sap at the beginning and end of the season both in the presence or absence of probiotics.

Furthermore, an organoleptic analysis was performed on samples that had an acceptable microbiological quality. In general, the enrichment of the maple products with both selected probiotic strains (*L. rhamnosus* and *B. lactis* Bb12) has not led to significant changes in the organoleptic and sensory characteristics of products.

The tests performed to study the physico-chemical, organoleptic and sensory analyses of maple products co-enriched with prebiotics were the same as those presented previously.

Higher concentrations (between 4.1 and 6% for the sap and concentrate maple respectively) were detected in samples containing symbiotic inulin, serum protein or mixture of both. This increase is simply due to the enrichment of samples by these prebiotic substances. No change was observed in the total solid content during the 30 days of the study Enrichment of the sap with inulin at a concentration of 2% was accompanied by a significant decrease in the pH (4) compared to pH near neutral (7) of sap with or without probiotics.

In addition, the sap prebiotic enrichment led to disappearance of the maple taste in the sap. To remedy this problem, commercial flavors of maple syrup to maximum concentration of 2% in the finished product, were used. The addition of these flavors made it possible to reproduce a characteristic taste of the sap without affecting the survival of probiotic strains added.

It may also be desirable to add a natural or artificial flavoring ingredient to the maple sap prior to the pasteurization step to provide a complementary flavor to the product. Fruit flavors have been found to be particularly advantageous for complementing the maple product and may include any one or combination of orange, apple, grapefruit, pineapple, strawberry, raspberry, cranberry, lime, lemon, grape, or peach, or any other suitable flavor, such as vanilla or chocolate that will enhance the refreshing quality of the beverage. Generally these ingredients will be added to the maple sap product in a flavoring amount, i.e., an amount that will not overpower the natural taste and flavor of the maple sap, which will generally be less than about 1% by volume of the final product.

Example 6

Effectiveness and Protective Effect of the Symbiotic Drink: In Vitro Study

Gastrointestinal Dynamic Simulator (TIM-1 Model)

The dynamic gastrointestinal TIM-1 model (TNO Nutrition and Food Research Institute, Zeist, Netherlands) was previously described by Minekus et al. (1995). The Model consists of four compartments simulating the stomach, duodenum, jejunum and ileum, which are connected by computer controlled peristaltic valve pumps. Each compartment is composed of two glass jackets, in which a flexible membrane is installed. The space between the membrane and the glass jacket is filled with warm water which helps to rise temperature of the chyme in each compartment to 37° C. The contractions of the flexible membranes are achieved by changing the pressure of the water. These contractions allows for imitating the peristaltic movements of the stomach and small intestine and thus mixing the chyme in each compartment. The contractions frequencies per minute are 5 and 6 times for gastric and duodenal compartments, respectively and 7 times/minute for jejunal and illeal compartments. During digestion, temperature is kept constantly at 37° C. and monitored by two independent sensors connected to the stomach and small intestine compartments. To imitate kidney function, two hallow fiber modules are connected to jejunal and illeal compartments. These modules allow for dialyzing the content of each compartment against small intestine electrolyte solution. The pHs in the gastric and small intestine compartments are monitored with four independent pH electrodes connected to the computer. Secretion of HCl in the gastric compartment or sodium bicarbonate in the small intestine compartments to control pH in various compartments is completely controlled and dosed via the computer.

Maple Sap Sample Preparation

Filtered pasteurized (as provided in Example 1) maple sap samples with or without added 2% inulin (as provided in Example 3) were inoculated with approximately $10^7$-$10^8$ cfu/ml of each of Lactobacillus rhamnosus and Bifidobacterium lactis (as provided in Example 2). Briefly, 300 g of the inoculated maple sap sample were then introduced into the stomach compartment of the TIM-1 model.

Sampling

During the first two hours of digestion, aliquots of 1 ml from the gastric compartment were taken at 0, 20, 40, 60 and 80 min to evaluate the impact of gastric environment on the viability of Lactobacillus and Bifidobacterium. Aliquots of 1 ml from duodenal compartment (at 30, 60, 90, 120 and 180 min) and from jejunal and illeal compartments (at 60, 120, 180, 240 and 300 min) were also taken for the same purpose. For the determination of illeal-delivered Lactobacillus rhamnosus and Bifidobacterium lactis, briefly 1 ml of illeal-delivered efflux was taken at 1 h intervals for microbiological analyses.

Microbiological Analyses

Serial 10-fold dilutions of each sample were made in peptone water (0.15%, w/v) and plated in duplicate onto Beerens agar and incubated an aerobically in jars using an atmosphere generation system (Oxoid AnaeroGen™, Oxoid Ltd., Basingstoke, Hampshire, England) at 37° C. for 48 h for the enumeration of Bifidobacterium lactis. For the enumeration of Lactobacillus rhamnosus, appropriate peptone water dilutions of each sample were plated in duplicate onto MRS-vancomycin agar (containing vancomycin at a concentration of 1 mg/l). Plates were incubated aerobically at 42° C. for 72 h.

Data Interpretation and Conclusion

Figure 2:
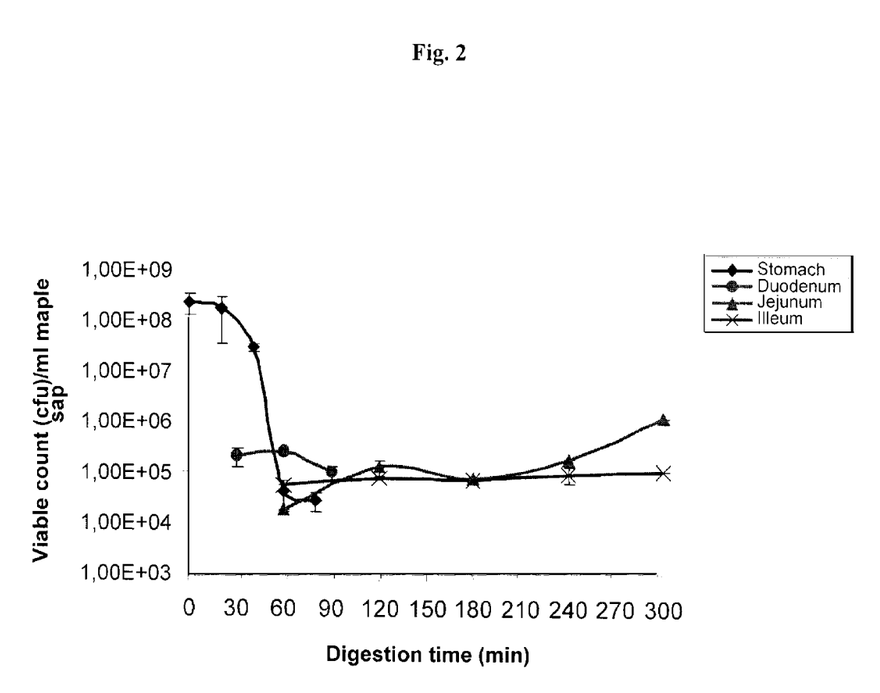
FIG. 2 is a graph showing the viability of *B. lactis* in gastrointestinal multicompartmental dynamic model (TIM-1) during digestion of maple sap sample without added inulin.
Figure 3:
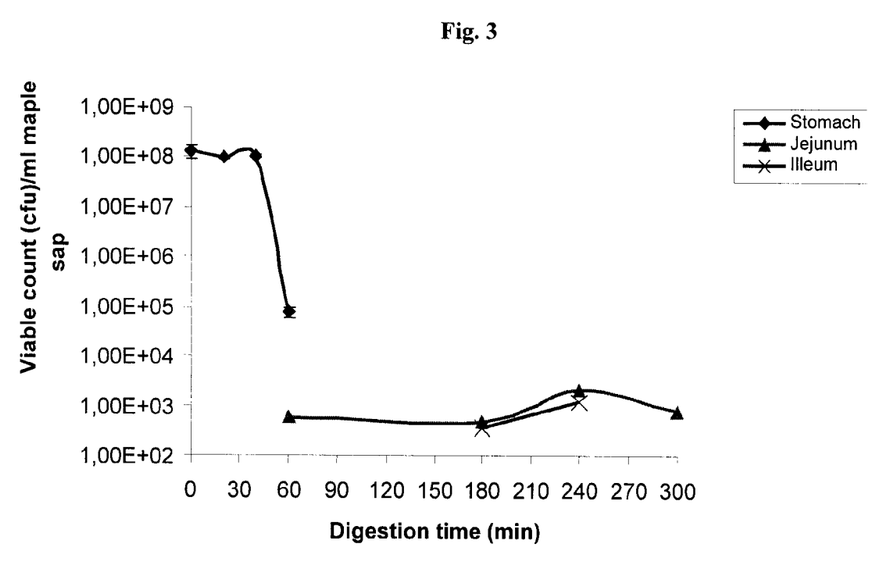
FIG. 3 is a graph showing the viability of *L. rhamnosus* in gastrointestinal multicompartmental dynamic model (TIM-1) during digestion of maple sap sample without added inulin.
Figure 4:
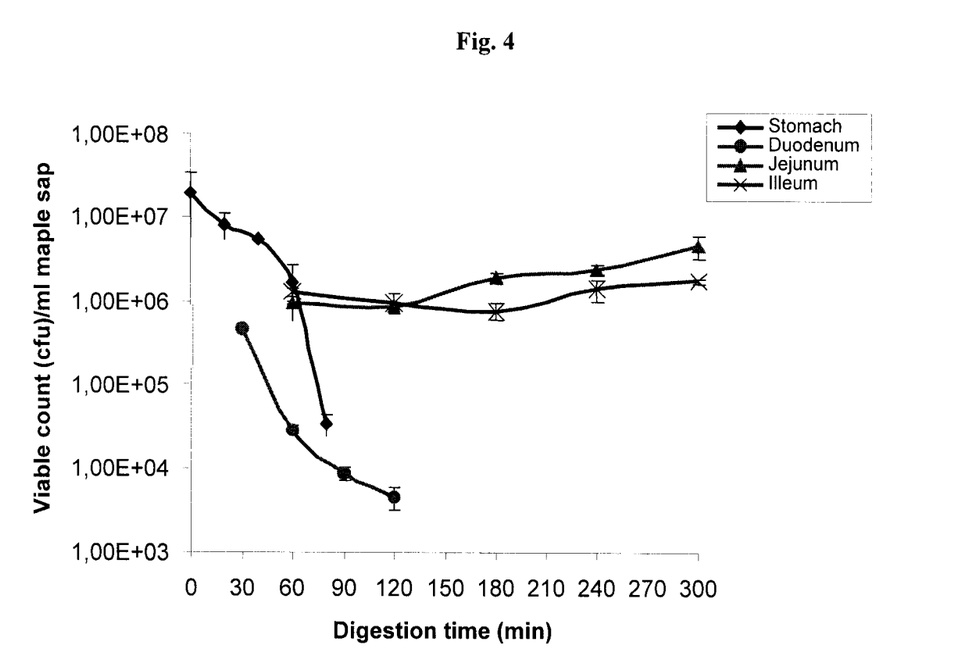
FIG. 4 is a graph showing the viability of *B. lactis* in gastrointestinal multicompartmental dynamic model (TIM-1) during digestion of maple sap sample with added 2% (w/v) inulin.
Figure 5:
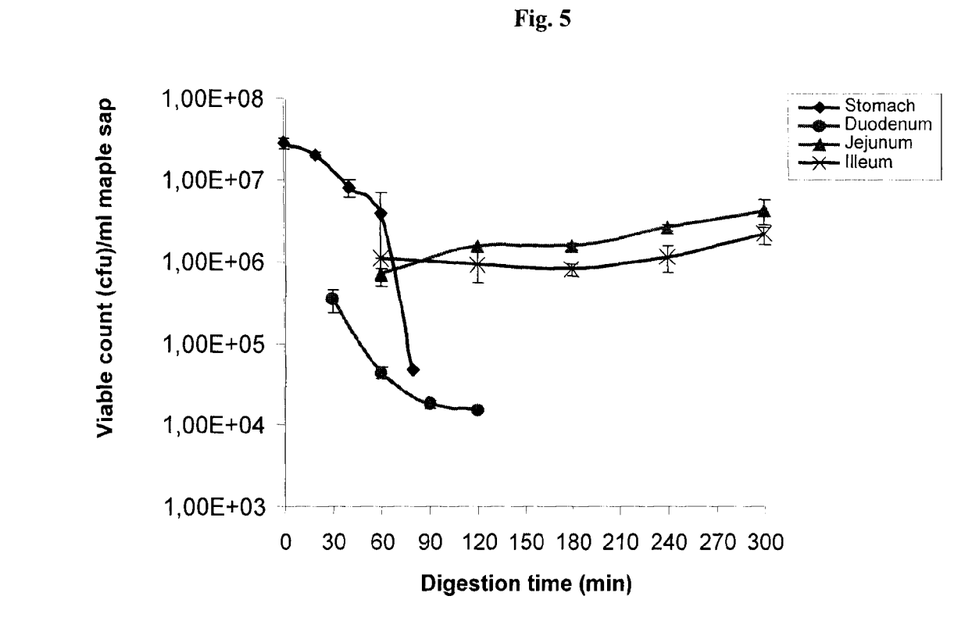
FIG. 5 is a graph showing the viability of *L. rhamnosus* in gastrointestinal multicompartmental dynamic model (TIM-1) during digestion of maple sap sample with added 2% (w/v) inulin.

The impact of gastrointestinal environment on the viability of Bifidobacterium lactis and Lactobacillus rhamnosus during in vitro digestion of maple sap samples without or with added 2% inulin is presented in FIGS. 2-5. The figures clearly illustrate that the viability of each organism is reduced remarkably in the gastric (due to acid secretion) and in the duodenal (due to bile secretion) compartments. However, such remarkable reductions in viability of such organism could not be observed in both jejunal or illeal compartments which may be attributing to acid neutralization and bile dilution that had been taken place in both compartments. On the other hand, Lactobacillus rhamnosus appeared to be more susceptible to bile than Bifidobacterium lactis, especially in maple sap samples without added inulin. This organism could not be detected in the duodenum compartment (FIG. 3). Inulin appeared to remarkably improve the tolerance of such organism to gastrointestinal stresses. Inulin contribution to the survival of L. rhamnosus and B. lactis can also be demonstrated by comparing FIGS. 2 and 4 for Bifidobacterium lactis and 3 and 5 for Lactobacillus rhamnosus. The count of such organisms determined in the ileal efflux was remarkably higher in samples with added inulin (FIGS. 4 and 5) compared with that without inulin (FIGS. 2 and 3). Without inulin the microorganisms survived in the TIM-1 at levels around $10^3$ to $10^4$ cfu. These levels of cfu may not be enough to exert health benefit. However, the addition of inulin contributed to the survival of the microorganisms in the TIM-1 to levels close to $10^7$ cfu, levels which are known in the art to exert health benefits. Therefore, this in vitro model suggests that in order to exert health benefits, the addition of inulin appears to be necessary for sap samples inoculated with levels of L. rhamnosus and B. lactis between $10^7$-$10^8$ cfu. Alternatively, in order to exert health benefits, the sap samples may be inoculated with L. rhamnosus and B. lactis at levels higher than $10^8$ cfu, for example at levels of $10^9$ or above.

We claim:

1. A composition suitable to be delivered to a mammalian gut, characterized in that the composition comprises:
   (a) a heat sterilized non-supplemented maple based medium including one or more of a maple sap, maple concentrate, maple syrup, and diluted maple syrup; and
   (b) at least one of a live exogenous probiotic, a prebiotic or a live exogenous probiotic-prebiotic combination, wherein said heat sterilized maple based medium is heat sterilized without altering an endogenous nutraceutical compound.

2. The composition as claimed in claim 1, wherein the heat sterilized non-supplemented maple based medium is a substrate for the live exogenous probiotic, or live exogenous probiotic-prebiotic combination.

3. The composition as claimed in claim 1, wherein the live exogenous probiotic is present in the composition in about $10^7$ cfu/ml to about $10^9$ cfu/ml.

4. The composition as claimed in claim 1, wherein the prebiotic is present in the composition in about up to 3% of the composition.

5. The composition as claimed in claim 1, characterized in that the live exogenous probiotic, the prebiotic, or the live exogenous probiotic-prebiotic combination, present in the heat sterilized non-supplemented maple based medium, is operable to achieve a shelf life of at least 45 days at 4° C.

6. The composition as claimed in claim 1, characterized in that the heat sterilized non-supplemented maple based medium is operable to promote the survival of the live exogenous probiotic, the prebiotic, or the live exogenous probiotic-prebiotic combination thereof in the composition, or product containing the composition.

7. The composition as claimed in claim 1, characterized in that the composition is a functional matrix for a beverage, a food, a preparation for application on skin or hair, a health drink, a mineralized drink, a soy milk based drink, a vinegar based drink, a vegetable based drink, a tea, a water containing food supplement, a tablet, a gel, a gel capsule, a lozenge, a pill, or a powder, containing probiotics, prebiotics, or a probiotic-prebiotic combinations.

8. The composition as claimed in claim 1, wherein said heat sterilized maple based medium is heat sterilized at a temperature of about 121° C. or less.

9. The composition as claimed in claim 1, wherein said heat sterilized maple based medium is heat sterilized at a temperature of about 121° C. for 15 minutes.

10. The composition as claimed in claim 1, wherein said heat sterilized maple based medium is heat sterilized at a temperature of about 63° C. for 20 minutes.

11. The composition as claimed in claim 1, wherein said heat sterilized maple based medium is heat sterilized at a temperature of about 80° C. for 10 minutes.

12. The composition as claimed in claim 1, wherein said heat sterilized maple based medium is heat sterilized at a temperature of about 55° C. for 30 minutes.

13. The composition as claimed of claim 1, wherein the heat sterilized maple based medium is further microfiltrated.

14. The composition as claimed in claim 1, wherein the heat sterilized maple based medium is further UV treated.

15. The composition as claimed in claim 1, wherein the exogenous probiotic is at least one of *Lactobacillus rhamnosus, Lactobacillus acidophilus, Lactobacillus plantarum, Lactobacillus reuteri, Lactobacillus curvatus, Lactobacillus bulgaricus, Lactobacillus grasseri, Lactobacillus casei, Lactobacillus fermentum, Lactobacillus caveasicus, Lactobacillus helveticus, Lactobacillus lactis, Lactobacillus salivarius, Lactobacillus brevis, Lactobacillus leichmanni, Lactobacillus cellobiosus, Lactobacillus buchneri, Bifidobacterium laterosporus, Bifidobacterium lactis* Bb12, *Bifidobacterium longum, Bifidobacterium breve, Bifidobacterium subtilus, Lactobacillus sporogenes, pediococcus acidilactici, pediococcus pentosaceus, enterococcus faecium, Bifidobacterium adolescentis, Bifidobacterium infantis, Bifidobacterium thermophilum, Bifidobacterium animalis, Bifidobacterium bifidum, Streptococcus thermophilius, Lactococcus lactis cremoris, S. Diacetylactis, S. Intermedius, enterococcus faecalis*, and butanoic acid bacterias.

16. The composition as claimed in claim 1, wherein the prebiotic is at least one of an oligosaccharide, a fructo-oligosaccharide, a pectin, a pectin polysaccharide, a mannan, a pentosan, a beta-glucan, and arabinan, a galactan, a serum peptide, or combinations thereof.

17. A method of producing a composition suitable to be delivered to a mammalian gut, the composition comprising at least one of a live exogenous probiotic, a prebiotic or a live exogenous probiotic-prebiotic combination and a heat sterilized non-supplemented maple based medium, characterized in that the method comprises the steps of:
 (a) inoculating a heat sterilized maple based medium with at least one of a live exogenous probiotic, a prebiotic or a live exogenous probiotic-prebiotic combination, such that the maple based medium acts as a protective matrix for the survival of the probiotic, prebiotic or probiotic-prebiotic combination.

18. The method as claimed in claim 17, wherein said heat sterilized non-supplemented maple based medium is heat sterilized at a temperature of about 63° C. for 20 minutes.

19. The method as claimed in claim 17, wherein said heat sterilized non-supplemented maple based medium is heat sterilized at a temperature of about 80° C. for 10 minutes.

20. The method as claimed in claim 17, wherein said heat sterilized non-supplemented maple based medium is heat sterilized at a temperature of about 55° C. for 30 minutes.

* * * * *